US007820666B2

(12) United States Patent
Harbeson

(10) Patent No.: US 7,820,666 B2
(45) Date of Patent: Oct. 26, 2010

(54) TETRAHYDROTRIAZOLOPYRAZINE DERIVATIVES AND USES THEREOF

(75) Inventor: Scott L. Harbeson, Cambridge, MA (US)

(73) Assignee: Concert Pharmaceuticals, Inc., Lexington, MA (US)

(*) Notice: Subject to any disclaimer, the term of this patent is extended or adjusted under 35 U.S.C. 154(b) by 0 days.

(21) Appl. No.: 12/116,475

(22) Filed: May 7, 2008

(65) Prior Publication Data

US 2008/0280913 A1 Nov. 13, 2008

Related U.S. Application Data

(60) Provisional application No. 60/916,704, filed on May 8, 2007.

(51) Int. Cl.
| | |
|---|---|
| A01N 43/58 | (2006.01) |
| A01N 43/60 | (2006.01) |
| A61K 31/50 | (2006.01) |
| A61K 31/495 | (2006.01) |
| C07D 471/00 | (2006.01) |
| C07D 487/00 | (2006.01) |
| C07D 491/00 | (2006.01) |
| C07D 495/00 | (2006.01) |
| C07D 497/00 | (2006.01) |

(52) U.S. Cl. ........................ 514/249; 544/350
(58) Field of Classification Search ........................ None
See application file for complete search history.

(56) References Cited

U.S. PATENT DOCUMENTS

| 5,304,121 | A | 4/1994 | Sahatjian |
| 5,886,026 | A | 3/1999 | Hunter et al. |
| 6,099,562 | A | 8/2000 | Ding et al. |
| 6,221,335 | B1 | 4/2001 | Foster |
| 6,303,661 | B1 | 10/2001 | Demuth et al. |
| 6,440,710 | B1 | 8/2002 | Keinan et al. |
| 6,603,008 | B1 | 8/2003 | Ando et al. |
| 6,699,871 | B2 | 3/2004 | Edmondson et al. |
| 6,803,031 | B2 | 10/2004 | Rabinowitz et al. |
| 7,517,990 | B2 | 4/2009 | Ito et al. |
| 2003/0100563 | A1 | 5/2003 | Edmondson et al. |
| 2004/0068141 | A1 | 4/2004 | Armstrong et al. |
| 2005/0032804 | A1 | 2/2005 | Cypes et al. |
| 2007/0082929 | A1 | 4/2007 | Gant et al. |
| 2007/0197695 | A1 | 8/2007 | Potyen et al. |
| 2007/0259927 | A1 | 11/2007 | Suzuki et al. |
| 2008/0039367 | A1 | 2/2008 | Izumi et al. |
| 2008/0103122 | A1 | 5/2008 | Veltri |
| 2009/0076013 | A1 | 3/2009 | Czarnik et al. |

FOREIGN PATENT DOCUMENTS

| EP | 1084705 A2 | 3/2001 |
| EP | 0896538 B1 | 7/2001 |
| EP | 1625847 A1 | 2/2006 |
| EP | 1412357 B1 | 3/2006 |
| EP | 1654263 B1 | 9/2007 |
| WO | WO 95/26325 A2 | 10/1995 |
| WO | WO 97/40832 A1 | 11/1997 |
| WO | WO03004498 | * 1/2003 |
| WO | WO 2004/085378 A1 | 10/2004 |
| WO | WO 2004/085661 A2 | 10/2004 |
| WO | WO 2004/087650 A2 | 10/2004 |
| WO | WO 2004/1130375 A2 | 12/2004 |
| WO | WO 2005/003135 A1 | 1/2005 |
| WO | WO 2006/011588 A1 | 2/2006 |
| WO | WO 2006/022428 A1 | 2/2006 |
| WO | WO 2006/119260 A2 | 11/2006 |
| WO | WO 2007/002374 A2 | 1/2007 |
| WO | WO 2007/037296 A1 | 5/2007 |
| WO | WO 2007/118651 | 10/2007 |

OTHER PUBLICATIONS http://en.wikipedia.org/wiki/Deuterium 9last checked on Sep. 21, 2009).*
Vincent, et. al., Drug Metabolism and Disposition; 35(4); (2007) pp. 538-8.*
Kushner, et. al.; Cnadian Journal of Physiology and Pharmacology; (1997) 77(2) pp. 79-88.*
Vincent, et. al., Drug Metabolism and Disposition (2007); vol. 35, No. 4, pp. 533-538.*
Park, et. al.; Annu. Rev. Pharmacol. Toxicol. 2001. 41:443-70.*
Kushner, et. al.; Canadian Journal of Physiology and Pharmacology; (1999), 77, 2, pp. 79-88.*
Wada E et al., Seikagaku 1994, 66: 15-28.
Gannes LZ et al., "Natural Abundance Variations in Stable Isotopes and their Potential Uses in Animal Physiology Ecology," Comp Biochem Physiol Mol Integr Physiol 1998, 119: 725-737.
Kim, D et.al., "(2R)-4-[3-(Trifluoromethyl)-5,6-dihydro[1,2,4]-triazolo[4,3-α]pyrazin-7(8H)-yl]-1- (2,4,5-trifluorophenyl)butan-2-amine: A Potent, Orally Active Dipeptidyl Peptidase IV Inhibitor for the Treatment of Type 2 Diabetes," J Med Chem, 2005, 48(1):141-151.
Hansen, BK et al., "First Generation Process for the Preparation of the DPP-IV Inhibitor Sitagliptin," Org Proc Res Develop, 2005, 9:634-639.
Sorbera, LA et al., 'MK-0431. Agent for Type 2 Diabetes Dipeptidyl-Peptidase IV (CD26) Inhibitor, Drugs Fut, 2005, 30(4):337-343.
O'Hagan, D. et al., "Efficient Routes to Isotopically Labelled Epichlorohydrins (Chloromethyl) oxiranes)," J. Labelled Comp and Radiopharmaceuticals, 1994, 34(9):871-880.
Wotiz, JH et al., "Mechanism of the base-catalyzed prototropic propargylic rearrangement in vicinal diamines," J Org Chem, 1973, 38(3):489-493.
Fontana, E et al., "Synthesis of Brostallicin (PNU-166196A) Labelled with $^2$H and $^{14}$C," J Labelled Comp and Radiopharmaceuticals, 2002, 45(11):899-909.

(Continued)

*Primary Examiner*—James O Wilson
*Assistant Examiner*—Jeffrey H Murray
(74) *Attorney, Agent, or Firm*—Woodcock Washburn LLP

(57) ABSTRACT

This invention relates to novel substituted tetrahydrotriazolopyrazines and their derivatives, pharmaceutically acceptable salts, solvates, and hydrates thereof. This invention also provides compositions comprising a compound of this invention and the use of such compositions in methods of treating diseases and conditions that are beneficially treated by administering an enzyme inhibitor of dipeptidyl-peptidase IV (DPP-IV).

19 Claims, No Drawings

OTHER PUBLICATIONS

Balaban, A. et al., "Regioselective deuteriation knetics of 2-, and 6-methyl groups in $D_2O$ solutions of pyrylium and N-methylpyridinium perchlorates possessing also 3-methyl or 3-phenyl groups," J Labelled Compd and Radiopharmaceuticals, 1982, 19(6):783-794.

Haedener, A et al., "Synthesis of Specifically Labelled L-Phenylalanines Using Phenylalanine Ammonia Lyase Activity," J Labelled Compd and Radiopharmaceuticals, 1987, 24(11):1291-1306.

Freireich, EJ et al., "Quantitative Comparison of Toxicity of Anticancer Agents in Mouse, Rat, Hamster, Dog, Monkey, and Man," (1966) Cancer Chemother. Rep 50: 219-244.

Obach, RS, "Prediction of human clearance of twenty-nine drugs from hepatic microsomal intrinsic clearance data: an examination of in vitro half-life approach and nonspecific binding to microsomes," Drug Metab Disp, 1999, 27:1350-1359.

Houston, JB et al., "Prediction of Hepatic Clearance from Microsomes, Hepatocytes, and Liver Slices," Drug Metab Rev, 1997, 29:891-922.

Houston, JB, "Utility of In Vitro Drug Metabolism Data in Predicting In Vivo Metabolic Clearance," Biochem Pharmacol, 1994, 47:1469-1479.

Iwatsubo, T et al., "Prediction of In Vivo Drug Metabolism in the Human Liver from In Vivo Metabolism Data," Pharmacol Ther, 1997, 73:147-171.

Lavé, T, et al., "The Use of Human Hepatocytes to Select Compounds Based on Their Expected Hepatic Extraction Ratios in Humans," Pharm Res, 1997, 14:152-155.

Vincent, S. H. et al., "Metabolism and Excretion of the Dipeptidyl Peptidase 4 Inhibitor [14C]Sitagliptin in Humans," Drug Metabolism and Disposition, Jan. 12, 2007, 35(4), 533-538.

Baillie, "The Use of Stable Isotopes in Pharmacological Research", Pharmacology Reviews, Jun. 1981, 33(2), 81-132 (In 2 Parts).

Browne, "Stable Isotope Techniques in Early Drug Development: An Economic Evaluation", J. Clin. Pharmacology, Mar. 1998, 38(3), 213-220.

Cherrah et al., "Study of Deuterium Isotope Effects on Protein Binding by Gas Chromatography/Mass Spectrometry. Caffeine and Deuterated Isotopomers", Biomed and Environmental Mass Spectrometry, Apr. 27, 1987, 14(11), 653-657.

Dyck et al., "Effects of Deuterium Substitution on the Catabolism of B-Phenylethylaine: An In Vivo Study", J. Neurochemistry, Feb. 1986, 46(2), 399-404.

Fisher et al., "The Complexities Inherent in Attempts to Decrease Drug Clearance by Blocking Sites of CYP-Mediated Metabolism", Current Opin. Drug Discov. Dev., Jan. 2006, 9(1), 101-109.

Foster, "Deuterium Isotope Effects in the Metabolism of Drugs and Xenobiotics: Implications for Drug Design", Adv. Drug Res., (no month available)1985, 14, 2-40.

Foster, "Deuterium Isotope Effects in Studies of Drug Metabolism", Trends in Pharmaceutical Sciences, Dec. 1984, 5, 524-527.

Gouyette, "Synthesis of Deuterium-Labelled Elliptinium and Its Use in Metabolic Studies", Biomed and Environmental Mass Spectrometry, Mar. 1, 1988, 15(5), 243-247.

Haskins, "The Application of Stable Isotopes in Biomedical Research", Biomed Spectrometry, Jul. 1982, 9(7), 269-277.

Honma et al., "The Metabolism of Roxatideine Acetate Hydrochloride—Liberation of Deuterium From The Piperidine Ring During Hydroxylation", Drug Metab. Dispos., Mar. 17, 1987, 15(4), 551-559.

Kushner et al., "Pharmacological Uses and Perspectives of Heavy Water and Deuterated Compounds", Can. J. Physiol. Pharmacol, Feb. 1999, 77(2), 79-88.

Pieniaszek et al., "Moricizine Bioavailability Via Simultaneous, Dual, Stable Isotope Administration: Bioequivalence Implications", J. Clin. Pharmacology, Aug. 1999, 39(8), 817-825.

Tonn et al., "Simultaneous Analysis of Diphenhydramine and a Stable Isotope Analog (2H10) Diphenhydramine Using Capillary Gas Chromatography with Mass Selective Detection in Biological Fluids from Chronically Instrumented Pregnant Ewes", Biol. Mass Spectrometry, Jul. 6, 1993, 22(11), 633-642.

Wolen, "The Application of Stable Isotopes to Studies of Drug Bioavailability and Bioequivalence", J. Clin. Phamacology, Jul. 1986, 26(6), 419-424.

* cited by examiner

TETRAHYDROTRIAZOLOPYRAZINE DERIVATIVES AND USES THEREOF

The present application claims priority to U.S. Provisional Application No. 60/916,704, filed May 8, 2007, entitled "TETRAHYDROTRIAZOLOPYRAZINE DERIVATIVES AND USES THEREOF", which is hereby incorporated by reference in their entirety.

FIELD OF THE INVENTION

This invention relates to novel substituted tetrahydrotriazolopyrazines and their derivatives, pharmaceutically acceptable salts, solvates, and hydrates thereof. This invention also provides compositions comprising a compound of this invention and the use of such compositions in methods of treating diseases and conditions that are beneficially treated by administering an enzyme inhibitor of dipeptidyl-peptidase IV (DPP-IV) and/or by increasing the hormone glucagon-like peptide-1 (GLP-1).

BACKGROUND OF THE INVENTION

Sitagliptin, known by the chemical name 3(R)-Amino-1-[3-(trifluoromethyl)-5,6,7,8-tetrahydro[1,2,4]triazolo[4,3-a]pyrazin-7-yl]-4-(2,4,5-trifluorophenyl)butan-1-one phosphate, modulates the enzyme dipeptidyl-peptidase IV (DPP-IV).

Sitagliptin is currently used in the treatment of Type II diabetes. It is also in clinical trials for lowering of fasting glucose levels.

Accordingly, it is desirable to provide a compound that has the beneficial activities of sitagliptin and may also have other benefits, e.g., reduced adverse side effects, with a decreased metabolic liability, to further extend its pharmacological effective life, enhance patient compliance and, potentially, to decrease population pharmacokinetic variability and/or decrease its potential for dangerous drug-drug interactions.

DETAILED DESCRIPTION OF ILLUSTRATIVE EMBODIMENTS

The terms "ameliorate" and "treat" are used interchangeably and include both therapeutic and prophylactic treatment. Both terms mean decrease, suppress, attenuate, diminish, arrest, or stabilize the development or progression of a disease (e.g., a disease or disorder delineated herein).

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of sitagliptin will inherently contain small amounts of deuterated and/or $^{13}$C-containing isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66: 15; Ganes L Z et al., Comp Biochem Physiol Mol Integr Physiol 1998, 119: 725. In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3000 (45% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

The term "isotopologue" refers to a species that differs from a specific compound of this invention only in the isotopic composition thereof.

The term "compound," as used herein, is also intended to include any salts, solvates or hydrates thereof.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention will include both racemic mixtures, and also individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

Both "$^2$H" and "D" refer to deuterium. "Stereoisomer" refers to both enantiomers and diastereomers. "US" refers to the United States of America.

Throughout this specification, a variable may be referred to generally (e.g., "each Y" or "each Y$^{2a}$") or may be referred to specifically (e.g., R$^1$, R$^{2a}$, Y$^{3b}$, etc.). Unless otherwise indicated, when a variable is referred to generally, it is meant to include all specific embodiments of that particular variable.

The present invention provides a compound of Formula I:

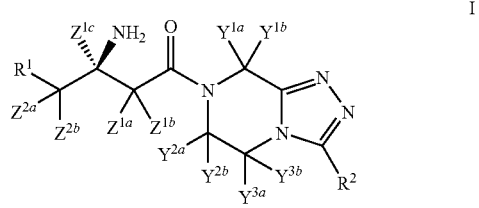

or a pharmaceutically acceptable salt thereof, wherein each Y variable is independently hydrogen or deuterium; each Z variable is independently hydrogen or deuterium; R$^1$ is a phenyl ring substituted with zero to three fluoro and zero to five deuterium groups; R$^2$ is CF$_3$, Cl, CH$_2$D, CHD$_2$, or CD$_3$; with the proviso that if each Y and Z variable is hydrogen and R$^1$ has zero deuterium, then R$^2$ comprises a deuterium atom.

In one embodiment R$^1$ is selected from 2,4,5-trifluorophenyl, 3,6-dideutero-2,4,5-trifluorophenyl, or 2,3,4,5,6-pentadeuterophenyl. In another embodiment R$^2$ is CF$_3$ or CD$_3$. In another embodiment R$^1$ is selected from 2,4,5-trifluorophenyl, 3,6-dideutero-2,4,5-trifluorophenyl, or 2,3,4,5,6-pentadeuterophenyl and R$^2$ is CF$_3$ or CD$_3$. In another embodiment R$^1$ is 2,4,5-trifluorophenyl. In another embodiment R$^1$ is 2,4,5-trifluorophenyl and R$^2$ is CF$_3$ or CD$_3$. In another embodiment R$^1$ is 2,4,5-trifluorophenyl and R$^2$ is CF$_3$.

In one embodiment each Y$^1$ variable is deuterium. In another embodiment each Y$^1$ and Z variable is deuterium. In another embodiment each Y$^2$ and Y$^3$ variable is deuterium. In another embodiment each Y$^2$, Y$^3$ and Z variable is deuterium. In another embodiment each Y and Z variable is deuterium.

In another embodiment each Y$^2$ variable is deuterium.

In another embodiment each Y$^3$ variable is deuterium.

In another embodiment each Z$^1$ variable is deuterium.

In another embodiment each Z$^2$ variable is deuterium.

In one embodiment R$^1$ is 2,4,5-trifluorophenyl and R$^2$ is CF$_3$. In another embodiment R$^1$ is 2,4,5-trifluorophenyl and R$^2$ is CF$_3$ and each Y$^1$ variable is deuterium. In another embodiment R$^1$ is 2,4,5-trifluorophenyl and R$^2$ is CF$_3$ and each Y$^1$ and Z variable is deuterium. In another embodiment R$^1$ is 2,4,5-trifluorophenyl and R$^2$ is CF$_3$ and each Y$^2$ and Y$^3$ variable is deuterium. In another embodiment R$^1$ is 2,4,5-trifluorophenyl and R$^2$ is CF$_3$ and each Y$^2$, Y$^3$ and Z variable is deuterium. In another embodiment each Y and Z variable is deuterium.

In another set of embodiments, in any of the aforementioned embodiments each variable that may be hydrogen or deuterium, and is not designated as deuterium, is hydrogen present at its natural isotopic abundance.

Examples of compounds of Formula I are shown in Table 1.

TABLE 1

Exemplary Compounds of Formula I (R¹-a)

(R¹-b)

(R¹-c)

| No. | R¹— | $Y^{1a}$ | $Y^{1b}$ | $Y^{2a}$ | $Y^{2b}$ | $Y^{3a}$ | $Y^{3b}$ | $Z^{1a}$ | $Z^{1b}$ | $Z^{1c}$ | $Z^{2a}$ | $Z^{2b}$ | R² |
|-----|-----|-----|-----|-----|-----|-----|-----|-----|-----|-----|-----|-----|-----|
| 100 | a | D | D | H | H | H | H | D | D | D | D | D | $CF_3$ |
| 101 | a | D | D | H | H | H | H | D | D | D | D | D | $CD_3$ |
| 102 | a | H | H | D | D | D | D | D | D | D | D | D | $CF_3$ |
| 103 | a | H | H | D | D | D | D | D | D | D | D | D | $CD_3$ |
| 104 | a | D | D | D | D | D | D | D | D | D | D | D | $CF_3$ |
| 105 | a | D | D | D | D | D | D | D | D | D | D | D | $CD_3$ |
| 106 | b | D | D | H | H | H | H | D | D | D | D | D | $CF_3$ |
| 107 | b | D | D | H | H | H | H | D | D | D | D | D | $CD_3$ |
| 108 | b | H | H | D | D | D | D | D | D | D | D | D | $CF_3$ |
| 109 | b | H | H | D | D | D | D | D | D | D | D | D | $CD_3$ |
| 110 | b | D | D | D | D | D | D | D | D | D | D | D | $CF_3$ |
| 111 | b | D | D | D | D | D | D | D | D | D | D | D | $CD_3$ |
| 112 | c | D | D | H | H | H | H | D | D | D | D | D | $CF_3$ |
| 113 | c | D | D | H | H | H | H | D | D | D | D | D | $CD_3$ |
| 114 | c | H | H | D | D | D | D | D | D | D | D | D | $CF_3$ |
| 115 | c | H | H | D | D | D | D | D | D | D | D | D | $CD_3$ |
| 116 | c | D | D | D | D | D | D | D | D | D | D | D | $CF_3$ |
| 117 | c | D | D | D | D | D | D | D | D | D | D | D | $CD_3$ |
| 118 | b | D | D | D | D | D | D | D | D | H | H | H | $CF_3$ |

In an even more specific embodiment, a compound of Formula I is Compound 118:

Compound 118

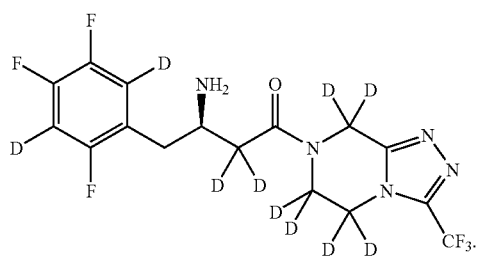

In another embodiment, any atom not designated as deuterium in any of the embodiments set forth above is present at its natural isotopic abundance.

The synthesis of compounds of Formula I can be readily achieved by synthetic chemists of ordinary skill. Relevant procedures and intermediates are disclosed, for instance in US2003100563; WO2004087650; WO2004085378; WO2004085661; US2005032804; WO2005003135; and EP1654263; and in Kim; D et. al., J Med Chem, 2005, 48(1): 141-151; and Hansen, B K et al., Org Proc Res Develop, 2005, 9:634-639.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Certain intermediates can be used with or without purification (e.g., filtration, distillation, sublimation, crystallization, trituration, solid phase extraction, and chromatography).

Convenient methods for synthesizing compounds of Formula I, or portions thereof, are depicted in Schemes I thru IV.

Scheme I: Synthesis of Deuterated Tetrahydrotriazolopyrazine Adduct XIX

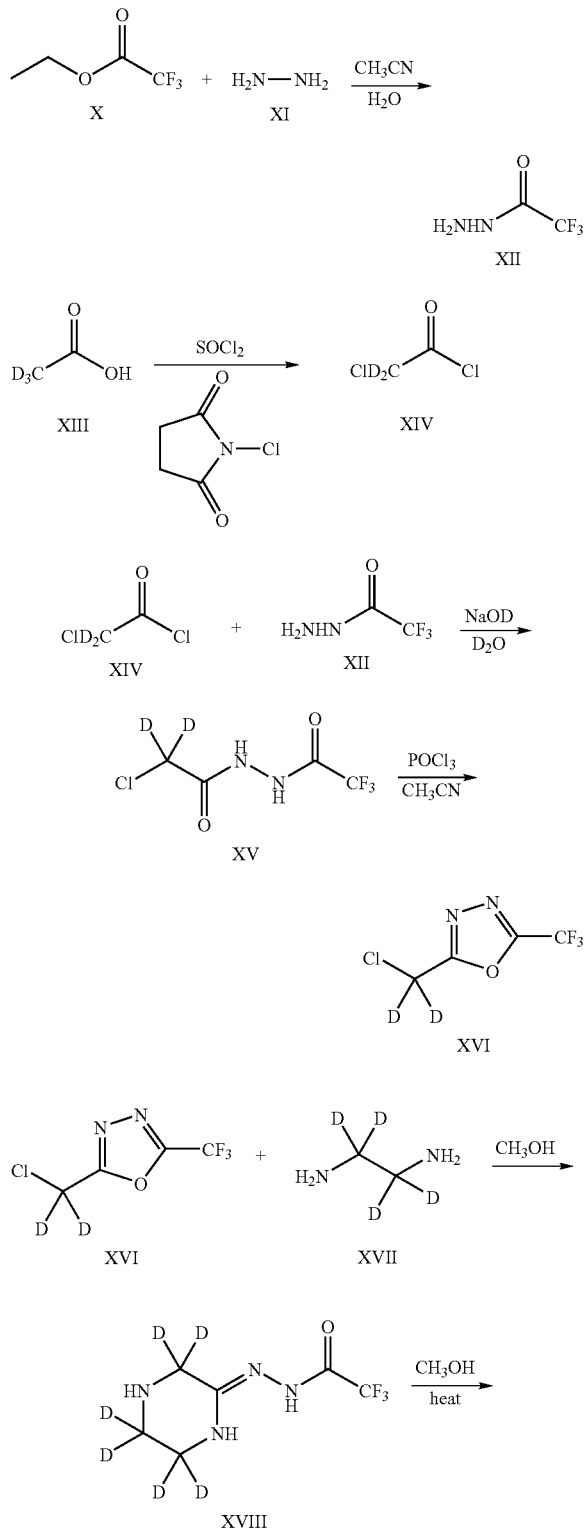

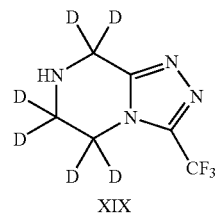

Curphey's reagent (X) is reacted with hydrazine (XI) to afford the monoacylated hydrazide derivative XII. Commercially available trideuterioacetic acid (XIII) is converted into the dideuterated chloroacetyl chloride derivative XIV by treatment with thionyl chloride in the presence of N-chlorosuccinimide. Compound XIV is then reacted with the monotrifluoroacetylated hydrazide (XII) to afford the deuterated diacylated hydrazide XV. Compound XV is then cyclized to the oxadiazole XVI by reaction with phosphorus oxychloride. The oxadiazole XVI is then treated with commercially available 1,1,2,2-tetradeuterio-1,2 diaminoethane XVII to produce the deuterated N-[(Z)-piperazin-2-ylidene]trifluoroacetohydrazide XVIII. Compound XVIII is then heated in methanol to finally afford the deuterated 3-(trifluoromethyl)-5,6,7,8-tetrahydro[1,2,4]triazolo[4,3-a]pyrazine XIX.

The procedures for the synthesis of the deuterated adduct XIX follow the published procedures for the non-deuterated adduct XIX. These procedures are described in the following papers: Kim, D et. al., J Med Chem, 2005, 48(1):141-151; Sorbera, L A et al., Drugs Fut, 2005, 30(4):337; and Hansen, B K et al., Org Process Res Dev, 2005, 9:634-639. The deuterated chloroacetyl chloride intermediate XIV is prepared as described by O'Hagan, D. et al., J. Labelled Comp and Radiopharmaceuticals, 1994, 34(9):871-880. Compound XVII is commercially available from Aldrich Chemical Co., Milwaukee, Wis. USA or can be synthesized by procedures described in Wotiz, J H et al., J Org Chem, 1973, 38(3):489-493; and in Fontana, E et al., J Labelled Comp and Radiopharmaceuticals, 2002, 45(11):899-909.

Scheme II: Synthesis of deuterated tetrahydrotriazolopyrazine adduct XXVI

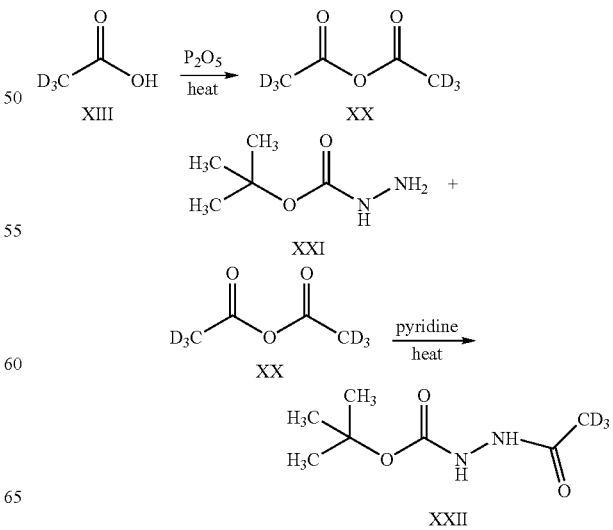

-continued

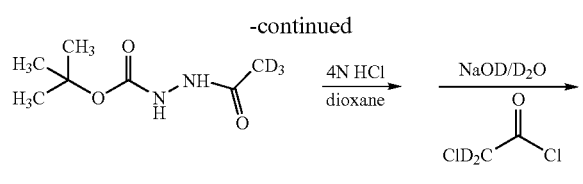

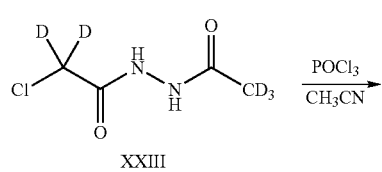

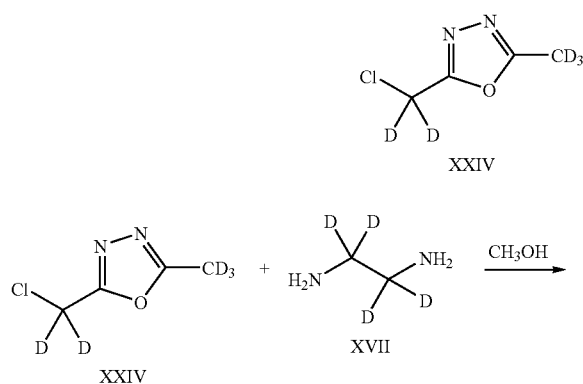

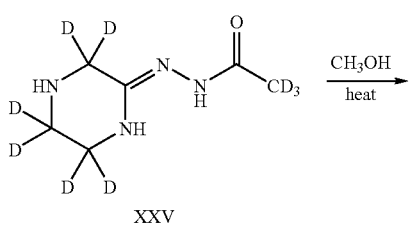

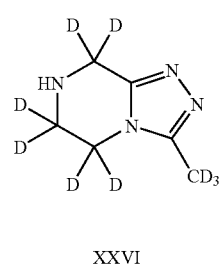

Trideuterated acetic acid (XIII) is dehydrated with heating in the presence of phosphorus pentoxide to form the deuterated anhydride XX which is then reacted with the monoprotected hydrazide XXI. Compound XXI is then acylated by reaction with compound XX to form the deuterated diacylated hydrazide adduct XXII. Compound XXII is then deprotected via treatment with 4N HCl/dioxane and is then acylated by reaction with deuterated chloroacetyl chloride XIV in the presence of NaOD/deuterium oxide to afford the deuterated bisacylated hydrazide XXIII. Compound XXIII is then cyclized to the deuterated oxadiazole derivative XXIV by treatment with phosphorus oxychloride. Compound XXIV is then reacted with commercially available 1,1,2,2-tetradeuterated-1,2-diaminoethane (XVII) to afford the deuterated N-[(Z)-piperazinyl-2-ylidene]trifluoroacetohydrazide XXV. Compound XXV is then heated to produce the deuterated 3-(trifluoromethyl)-5,6,7,8-tetrahydro[1,2,4]triazolo[4,3-a]pyrazine XXVI adduct. The procedures for the synthesis of the deuterated adduct XXVI follow the published procedures for the non-deuterated adduct XXVI. These procedures are described in the following papers: Kim, D et. al., J Med Chem, 2005, 48(1):141-151; Sorbera, L A et al., Drugs Fut, 2005, 30(4):337; and Hansen, B K et al., Org Process Res Dev, 2005, 9:634-639.

Scheme III: Synthesis of deuterated Beta Amino Acid precursor XXXIV

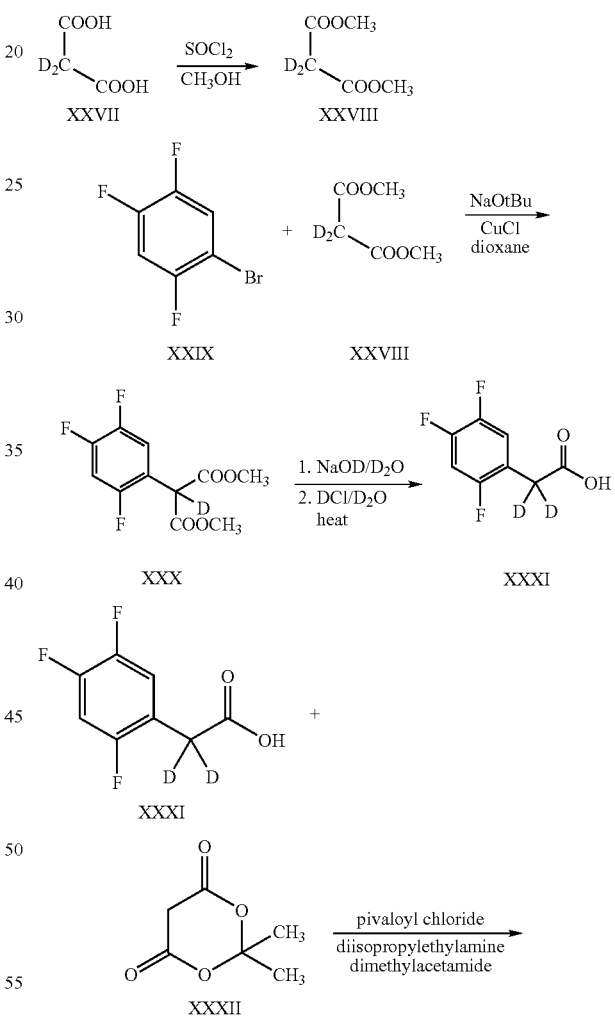

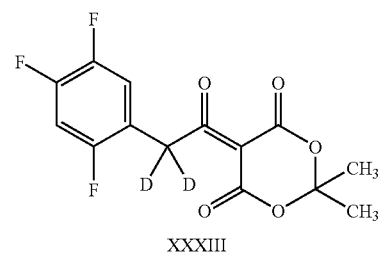

-continued

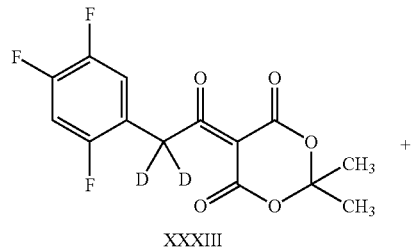

XXXIII

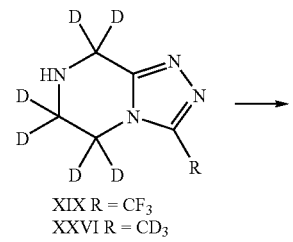

XIX R = CF$_3$
XXVI R = CD$_3$

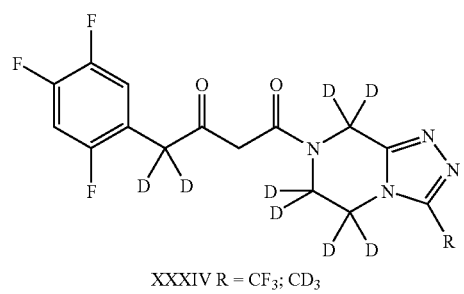

XXXIV R = CF$_3$; CD$_3$

The dideuterated malonic acid adduct XXVII is then reacted with thionyl chloride in methanol to produce the deuterated dimethyl malonate adduct XXVIII. The malonate adduct XXVIII is then coupled to 1-bromo-2,4,5-trifluorobenzene (XXIX) in the presence of NaOtBu and CuCl in dioxane to produce the deuterated malonate intermediate XXX which is then saponified (NaOD/deuterium oxide) and decarboxylated (DCl/deuterium oxide) to afford the dideuterated phenylacetic acid derivative XXXI. Compound XXXI is then coupled with Meldrum's acid (XXXII) in the presence of pivaloyl chloride and diisopropylethylamine to produce the deuterated adduct XXXIII. Finally, Compound XXXIII is reacted with either deuterated tetrahydrotriazolopyrazine XIX (Scheme I) or deuterated tetrahydrotriazolopyrazine XXVI (Scheme II) to produce the deuterated beta amino acid precursor XXXIV. The procedures for the synthesis of the deuterated adduct XXXIV follow the published procedures for the non-deuterated adduct XXXIV. These procedures are described in the following papers: Kim, D et. al., J Med Chem, 2005, 48(1):141-151; Sorbera, L A et al., Drugs Fut, 2005, 30(4):337; and Hansen, B K et al., Org Process Res Dev, 2005, 9:634-639. The dideuterated malonic acid derivative XXVII is prepared by the methods described in Balaban, A. et al., J Labelled Compd and Radiopharmaceuticals, 1982, 19(6):783-794 and in Haedner, A et al., J Labelled Compd and Radiopharmaceuticals, 1987, 24(11):1291-1306. The deuterated phenylacetic acid intermediate XXXI is prepared as described in United States Patent Publication 20040068141.

Scheme IV: Synthesis of a Compound of Formula I

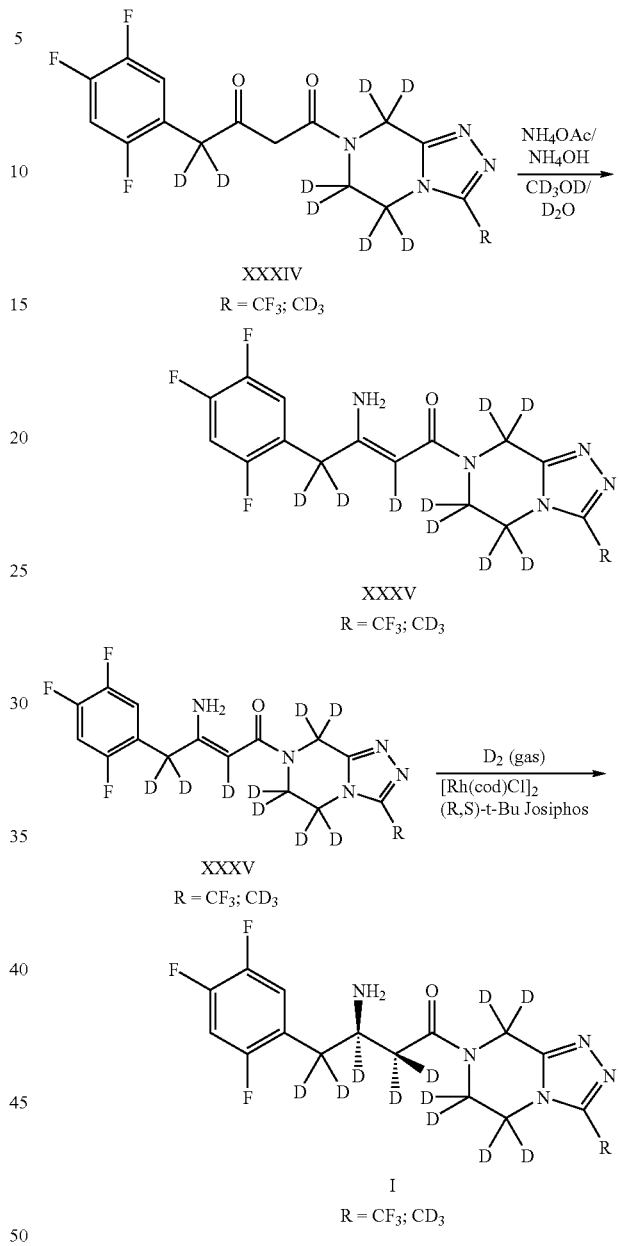

Deuterated compound XXXIV is then treated with ammonium acetate and ammonium hydroxide in the presence of d4-methanol and deuterium oxide which results in formation of enamine adduct XXXV. Compound XXXV is then subjected to asymmetric deuteriogenation using deuterium gas in the presence of a Rhodium dichlorocyclooctadiene catalyst and a chiral phosphine ligand (R,S)-t-Bu Josiphos to afford a compound of Formula I. The procedures for the synthesis of the deuterated adduct XXXVI follow the published procedures for the non-deuterated adduct XXXVI. These procedures are described in the following papers: Kim, D et. al., J Med Chem, 2005, 48(1):141-151; Sorbera, L A et al., Drugs Fut, 2005, 30(4):337; and Hansen, B K et al., Org Process Res Dev, 2005, 9:634-639.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, etc.) or not. The suitability of a chemical group in a compound structure for use in the synthesis of another compound is within the knowledge of one of ordinary skill in the art. Additional methods of synthesizing compounds of Formula I and their synthetic precursors, including those within routes not explicitly shown in schemes herein, are within the means of chemists of ordinary skill in the art. Methods for optimizing reaction conditions and, if necessary, minimizing competing by-products, are known in the art. In addition to the synthetic references cited herein, reaction schemes and protocols may be determined by the skilled artisan by use of commercially available structure-searchable database software, for instance, SciFinder® (CAS division of the American Chemical Society), STNR® (CAS division of the American Chemical Society), CrossFire Beilstein® (Elsevier MDL), or internet search engines such as Google® or keyword databases such as the US Patent and Trademark Office text database.

The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, $3^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

The invention also provides pyrogen-free compositions comprising an effective amount of a compound of Formula I (e.g., including any of the formulae herein), or a pharmaceutically acceptable salt, solvate, or hydrate of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the patient therapeutics may be local, so as to be administered at the site of interest. Various techniques can be used for providing the patient compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as sitagliptin. Such agents include those indicated as being useful in combination with sitagliptin, including but not limited to, those described in US2003100563; WO20041130375; EP1635832; EP0896538; EP1084705; WO1997040832; U.S. Pat. No. 6,303,661; EP1412357; EP1625847; U.S. Pat. No. 6,699,871; US2003100563; WO200702374; WO2006119260; WO2006022428; WO2006011588; and WO2007037296.

Preferably, the second therapeutic agent is an agent useful in the treatment or prevention of a disease or condition selected from Type II diabetes; metabolic syndrome X; reactive hypoglycemia; abnormal fasting glucose levels; diabetic dyslipidemia; obesity; hyperlipidemia; hypertriglyceridemia; hypercholesteremia; low LDL levels; high HDL levels; atherosclerosis; vascular restenosis; irritable bowel syndrome; inflammatory bowel disease including Crohn's Disease and ulcerative colitis; inflammatory conditions; pancreatitis; abdominal obesity; neurodegenerative disease; retinopathy; nephropathy; neuropathy; polycystic ovarian syndrome; and other diseases where insulin resistance is a component.

In one embodiment, the second therapeutic agent is a PPAR gamma agonist or metformin.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from 0.5 mg/day to 2000 mg/day for an adult human; from 5 mg/day to 1000 mg/day for an adult human; from 10 mg/day to 400 mg/day for an adult human; or from 50 mg/day to 200 mg/day for an adult human.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for sitagliptin.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

In another embodiment, the invention provides a method of modulating the activity of the enzyme dipeptidyl peptidase IV (DPP-IV) in a cell, comprising contacting a cell with one or more compounds of Formula I herein.

According to another embodiment, the invention provides a method of treating a patient suffering from, or susceptible to, a disease that is beneficially treated by sitagliptin comprising the step of administering to said patient an effective amount of a compound or a composition of this invention. Such diseases are well known in the art and are disclosed in, but not limited to the following patents and published applications: US2003100563

Such diseases include, but are not limited to Type II Diabetes; metabolic syndrome X; reactive hypoglycemia; abnormal fasting glucose levels; diabetic dyslipidemia; obesity; hyperlipidemia; hypertriglyceridemia; hypercholesteremia; low LDL levels; high HDL levels; atherosclerosis; vascular restenosis; irritable bowel syndrome; inflammatory bowel disease including Crohn's Disease and ulcerative colitis; inflammatory conditions; pancreatitis; abdominal obesity; neurodegenerative disease; retinopathy; nephropathy; neuropathy; polycystic ovarian syndrome; and other diseases where insulin resistance is a component.

In one particular embodiment, the method of this invention is used to treat a patient suffering from or susceptible to a disease or condition selected from Type II diabetes and obesity.

In another particular embodiment, the method of this invention is used to treat a patient suffering from or susceptible to Type II Diabetes.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to the patient one or more second therapeutic agents. The choice of second therapeutic agent may be made from any second therapeutic agent known to be useful for co-administration with sitagliptin. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I with metformin or a PPAR gamma agonist to treat a patient susceptible to or suffering from Type II diabetes.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I for use in the treatment or prevention in a patient of a disease, disorder or symptom thereof delineated herein.

The compounds and compositions of this invention are also useful as reagents in methods for determining the concentration of sitagliptin in solution or biological sample such as plasma, examining the metabolism of sitagliptin and other analytical studies.

According to one embodiment, the invention provides a method of determining the concentration, in a solution or a biological sample, of sitagliptin, comprising the steps of:

a) adding a known concentration of a compound of Formula I to the solution of biological sample;

b) subjecting the solution or biological sample to a measuring device that distinguishes sitagliptin from a compound of Formula I;

c) calibrating the measuring device to correlate the detected quantity of the compound of Formula I with the known concentration of the compound of Formula I added to the biological sample or solution; and d) measuring the quantity of sitagliptin in the biological sample with said calibrated measuring device; and e) determining the concentration of sitagliptin in the solution of sample using the correlation between detected quantity and concentration obtained for a compound of Formula I.

Measuring devices that can distinguish sitagliptin from the corresponding compound of Formula I include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula I comprising the steps of contacting the compound of Formula I with a metabolizing enzyme source for a period of time and comparing the amount of the compound of Formula I with the metabolic products of the compound of Formula I after the period of time.

In a related embodiment, the invention provides a method of evaluating the metabolic stability of a compound of Formula I in a patient following administration of the compound of Formula I. This method comprises the steps of obtaining a serum, urine or feces sample from the patient at a period of time following the administration of the compound of Formula I to the subject; and comparing the amount of the compound of Formula I with the metabolic products of the compound of Formula I in the serum, urine or feces sample.

The present invention also provides kits for use to treat Type II Diabetes or obesity. These kits comprise (a) a pharmaceutical composition comprising a compound of Formula I or a salt, hydrate, or solvate thereof, wherein said pharmaceutical composition is in a container; and (b) instructions describing a method of using the pharmaceutical composition to treat Type II Diabetes or obesity.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of (R)-3-(tert-butoxycarbonylamino)-4-(2,4,5-trifluoro-3,6-$d_2$-phenyl)-2,2-$d_2$-butanoic acid (12). Intermediate 12 was prepared as outlined in Scheme V below. Details of the synthesis are set forth below.

Scheme V: Preparation of Intermediate 12.

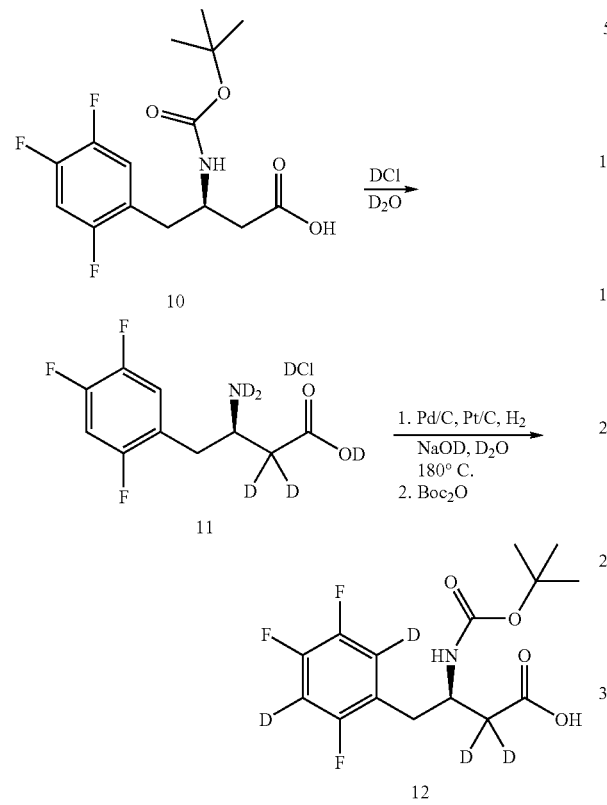

Synthesis of (R)-3-(amino-d$_2$)-4-(2,4,5-trifluorophenyl)-2,2-d$_2$-butanoic acid (11). To a heavy walled glass pressure vessel charged with Boc-(R)-3-amino-4-(2,4,5-trifluorophenyl)-butyric acid 10 (4.00 g, 12.0 mmol) and D$_2$O (19.0 mL) was added DCl (9.00 mL of a 12M solution in D$_2$O). The reaction was then heated to 70° C. at which time dissolution of the amino acid occurred. The pressure vessel was then sealed and the reaction stirred at 160° C. for 15 h. After cooling to room temperature the contents of the vessel were frozen and the D$_2$O removed via lyophilization to afford 11 (3.13 g, 95%) as a white crystalline solid. MS (M+H): 236.1 (ND$_2$ and COOD fully exchanged).

Synthesis of (R)-3-(tert-butoxycarbonylamino)-4-(2,4,5-trifluoro-3,6-d$_2$-phenyl)-2,2-d$_2$-butanoic acid (12). To a heavy walled glass pressure vessel charged with 11 (1.50 g, 5.44 mmol) and D$_2$O (90.0 mL) was added NaOD (until the solution achieved pH >8). 10% Pd/C (150 mg, 10 wt %) was then added followed by 5% Pt/C (300 mg, 20 wt %). The vessel was then purged several times with N$_2$ followed by H$_2$ before allowing the reaction to stir under an H$_2$ atmosphere (1 atmosphere) for 10-15 min. The vessel was then purged with N$_2$, sealed, and the reaction stirred at 180° C. for 15 h. Upon cooling to room temperature, the reaction was filtered through Celite®, and washed with D$_2$O (approximately 30.0 mL). To this solution was added di-tert butyl dicarbonate (1.79 g, 8.23 mmol) followed by THF (5.00 mL). After stirring for 15 h at room temperature, the reaction mixture was brought to pH <7 with 1M HCl and extracted with ethyl acetate (3×200 mL). The organic layers were combined, washed with brine, dried (MgSO$_4$), filtered and concentrated in vacuo to afford 12 (1.40 g, 66%) as an off-white solid. MS (M−H): 336.1.

Example 2

Synthesis of 5,5,6,6,8,8-d$_6$-3-(trifluoromethyl)-5,6,7,8-tetrahydro-[1,2,4]triazolo[4,3-a]pyrazine (XIX). Intermediate XIX was prepared as outlined in Scheme VI below. Details of the synthesis are set forth below.

Scheme VI: Preparation of Intermediate XIX.

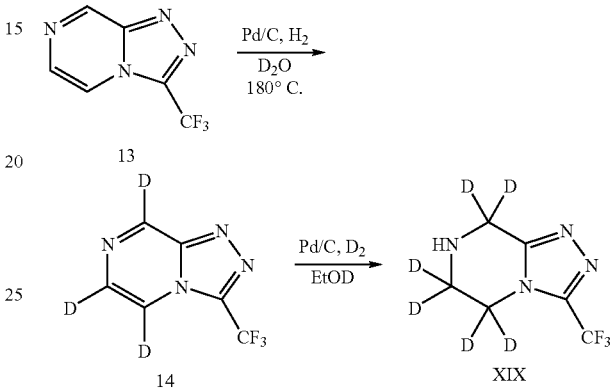

Synthesis of 5,6,8-d$_3$-3-(trifluoromethyl)-[1,2,4]triazolo[4,3-a]pyrazine (14). To a heavy walled glass pressure vessel charged with 3-(trifluoromethyl)-[1,2,4]triazolo[4,3-a]pyrazine 13 (2.00 g, 10.6 mmol) and D$_2$O (81.0 mL) was added 10% Pd/C (400 mg, 20 wt %). The vessel was then purged several times with N$_2$ followed by H$_2$ before allowing the reaction to stir under an H$_2$ atmosphere (1 atmosphere) for 10-15 min. The vessel was then purged with N$_2$, sealed, and the reaction stirred at 180° C. for 15 h. At this time additional D$_2$O (5.00 mL) and 10% Pd/C (400 mg, 20 wt %) were added and the vessel was again purged several times with N$_2$ followed by H$_2$ before allowing the reaction to stir under an H$_2$ atmosphere (1 atmosphere) for 10-15 min. The vessel was then purged with N$_2$, sealed, and the reaction stirred at 180° C. for an additional 15 h. Upon cooling to room temperature the reaction was filtered through Celite® which was subsequently washed several times with ethyl acetate and water (alternating washes). The dark brown solution was then brought to pH >7 with saturated aqueous sodium bicarbonate, and extracted with ethyl acetate (3×200 mL). The organic layers were combined, washed with brine, dried (MgSO$_4$), filtered and concentrated in vacuo to afford a dark brown oil. Purification via flash chromatography (gradient elution, 0-40% ethyl acetate/hexanes) afforded 14 (530 mg, 26%) as a brown crystalline solid. MS (M+H): 192.1.

Synthesis of 5,5,6,6,8,8-d$_6$-3-(trifluoromethyl)-5,6,7,8-tetrahydro-[1,2,4]triazolo[4,3-a]pyrazine (XIX). To a solution of 14 (530 mg, 2.77 mmol) in ethanol-d (15.0 mL) was added 10% Pd/C (53.0 mg, 10 wt %). The flask was then purged several times with N$_2$ followed by D$_2$ before allowing the reaction to stir under a D$_2$ atmosphere (1 atmosphere) for 15 h. The reaction was then purged with N$_2$ and filtered through Celite® which was subsequently washed with ethanol-d. The resulting solution was then concentrated in vacuo and purified via flash chromatography (gradient elution, 0-5% methanol/DCM) to afford XIX (300 mg, 55%) as a brown oil. MS (M+H): 199.1.

Example 3

(R)-3-amino-1-(5,5,6,6,8,8-d$_6$-3-(trifluoromethyl)-5,6-dihydro-[1,2,4]triazolo[4,3-a]pyrazin-7(8H)-yl)-4-(2,4,5-trifluoro-3,6-d$_2$-phenyl)-2,2-d$_2$-butan-1-one (118). Compound 118 was prepared according to Scheme VII below. Details of the synthesis are set forth below.

Scheme VII: Preparation of Compound 118.

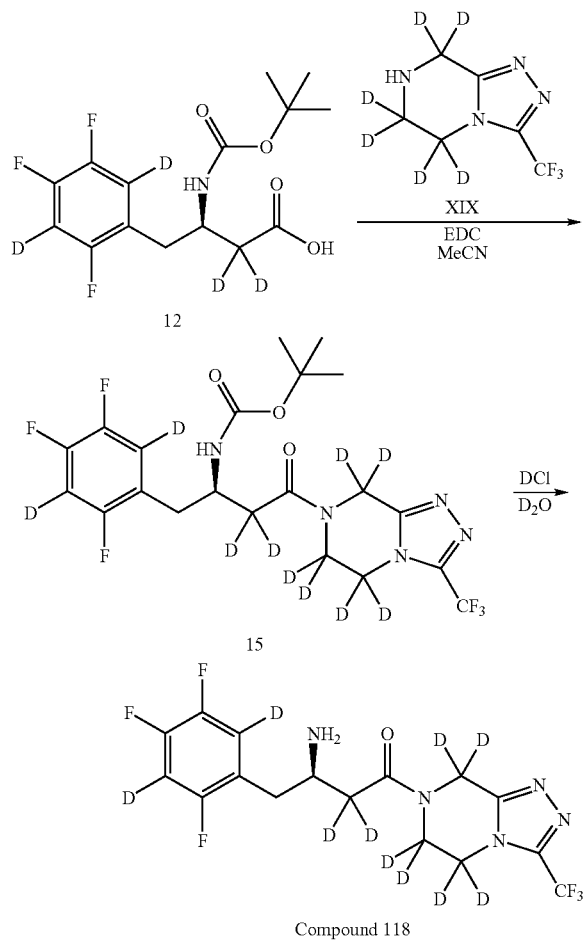

Compound 118

Synthesis of (R)-tert-butyl 4-oxo-4-(5,5,6,6,8,8-d$_6$-3-(trifluoromethyl)-5,6-dihydro-[1,2,4]triazolo[4,3-a]pyrazin-7(8H)-yl)-1-(2,4,5-trifluoro-3,6-d$_2$-phenyl)2,2-d$_2$-butan-2-yl-carbamate (15). To a solution of 12 (202 mg, 0.599 mmol) and XIX (149 mg, 0.750 mmol) in acetonitrile (6.00 mL) was added EDC-HCl (172 mg, 0.899 mmol). The reaction mixture was stirred at room temperature for 3 h at which time water (100 mL) was added. The reaction was then extracted with ethyl acetate (3×100 mL). The organic layers were then combined, washed with brine, dried (MgSO$_4$), filtered and concentrated in vacuo. The resulting material was purified via HPLC (Agilent C-18 prep column (21.2×50 mm), flow rate=20 mL/min, gradient elution: 5-95% ACN (0.1% formic acid)/Water (0.1% formic acid), retention time=6.96 min) to afford 15 (60.0 mg, 19%) as a white solid MS (M+H−t-Bu): 462.1.

Synthesis of (R)-3-amino-1-(5,5,6,6,8,8-d$_6$-3-(trifluoromethyl)-5,6-dihydro-[1,2,4]triazolo[4,3-a]pyrazin-7(8H)-yl)-4-(2,4,5-trifluoro-3,6-d$_2$-phenyl)-2,2-d$_2$-butan-1-one (Compound 118). To a solution of 15 (60.0 mg, 0.116 mmol) in D$_2$O (1.20 mL) was added DCl (600 μL of a 12M solution in D$_2$O). The reaction mixture was stirred at room temperature for 1 h at which time the contents were frozen and the D$_2$O removed by lyophilization. The resulting white solid was then dissolved in methanol and concentrated in vacuo (repeated several times) in order to effect proton exchange of the ND$_2$ and DCl to afford Compound 118 (51.0 mg, 97%) as a white solid. $^1$H NMR (400 MHz, CD$_3$OD) δ 3.90 (br. s., 1H); 3.10 (br. s., 2H); MS (M+H): 418.1.

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Twatsubo, T et al., Pharmacol Ther, 1997, 73:147; and Lave, T, et al., Pharm Res, 1997, 14:152.

Microsomal Assay: The metabolic stability of compounds of Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Experimental Procedures: Human liver microsomes are obtained from a commercial source (e.g., Absorption Systems L.P. (Exton, Pa.)). The incubation mixtures are prepared as follows:

Reaction Mixture Composition

| | |
|---|---|
| Liver Microsomes | 1.0 mg/mL |
| NADPH | 1 mM |
| Potassium Phosphate, pH 7.4 | 100 mM |
| Magnesium Chloride | 10 mM |
| Test Compound | 1 μM. |

Incubation of Test Compounds with Liver Microsomes: The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 μM. An aliquot of the reaction mixture is prepared as a blank control, by the addition of plain organic solvent (not the test compound). The reaction is initiated by the addition of cofactors (not into the negative controls), and then incubated in a shaking water bath at 37° C. Aliquots (200 μL) are withdrawn in triplicate at multiple time points (e.g., 0, 15, 30, 60, and 120 minutes) and combined with 800 μL of ice-cold 50/50 acetonitrile/dH$_2$O to terminate the reaction. The positive controls, testosterone and propranolol, as well as sitagliptin, are each run simultaneously with the test compounds in separate reactions.

All samples are analyzed using LC-MS (or MS/MS). An LC-MRM-MS/MS method is used for metabolic stability. Also, Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed:

1. A compound of formula I:

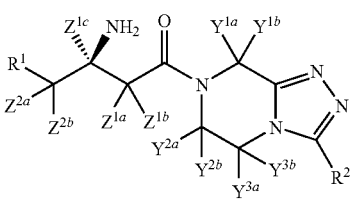

or a pharmaceutically acceptable salt thereof, wherein:
each Y variable is independently hydrogen or deuterium;
each Z variable is independently hydrogen or deuterium;
$R^1$ is 2,3,4,5,6-pentadeuterophenyl; and
$R^2$ is $CF_3$, Cl, $CH_2D$, $CHD_2$ or $CD_3$.

2. The compound of claim 1 where $R^2$ is selected from $CF_3$ or $CD_3$.

3. The compound of claim 2 where each $Y^1$ variable is deuterium.

4. The compound of claim 2 where each Z variable is deuterium.

5. The compound of claim 2 where each $Y^1$ and Z variable is deuterium.

6. The compound of claim 2 where each $Y^2$ and $Y^3$ variable is deuterium.

7. The compound of claim 6 where each $Y^2$, $Y^3$ and Z variable is deuterium.

8. The compound of claim 2 where each Y and Z variable is deuterium.

9. A compound of formula I:

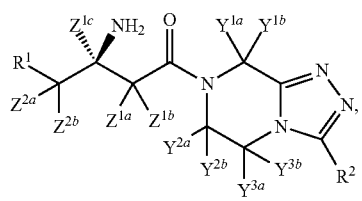

selected from any one of the compounds in the table below, wherein

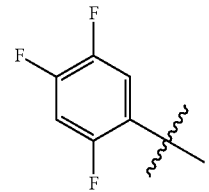

represents $R^1$-a,

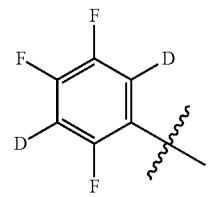

represents $R^1$-b, and

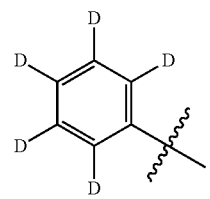

represents $R^1$-c:

| No. | $R^1$— | $Y^{1a}$ | $Y^{1b}$ | $Y^{2a}$ | $Y^{2b}$ | $Y^{3a}$ | $Y^{3b}$ | $Z^{1a}$ | $Z^{1b}$ | $Z^{1c}$ | $Z^{2a}$ | $Z^{2b}$ | $R^2$ |
|---|---|---|---|---|---|---|---|---|---|---|---|---|---|
| 101 | a | D | D | H | H | H | H | D | D | D | D | D | $CD_3$ |
| 103 | a | H | H | D | D | D | D | D | D | D | D | D | $CD_3$ |
| 105 | a | D | D | D | D | D | D | D | D | D | D | D | $CD_3$ |
| 107 | b | D | D | H | H | H | H | D | D | D | D | D | $CD_3$ |
| 109 | b | H | H | D | D | D | D | D | D | D | D | D | $CD_3$ |
| 111 | b | D | D | D | D | D | D | D | D | D | D | D | $CD_3$ |
| 112 | c | D | D | H | H | H | H | D | D | D | D | D | $CF_3$ |
| 113 | c | D | D | H | H | H | H | D | D | D | D | D | $CD_3$ |
| 114 | c | H | H | D | D | D | D | D | D | D | D | D | $CF_3$ |
| 115 | c | H | H | D | D | D | D | D | D | D | D | D | $CD_3$ |
| 116 | c | D | D | D | D | D | D | D | D | D | D | D | $CF_3$ |
| 117 | c | D | D | D | D | D | D | D | D | D | D | D | $CD_3$ | or a pharmaceutically acceptable salt thereof.

10. A compound of formula I:

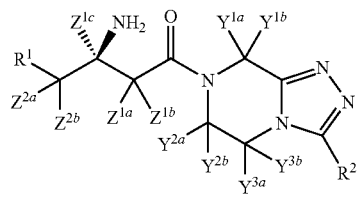

or a pharmaceutically acceptable salt thereof, wherein:
each Y variable is independently hydrogen or deuterium;
each Z variable is independently hydrogen or deuterium;

$R^1$ is selected from 2,4,5-trifluorophenyl; 3,6-dideutero-2,4,5-trifluorophenyl; or 2,3,4,5,6-pentadeuterophenyl; and $R^2$ is $CH_2D$, $CHD_2$ or $CD_3$.

11. The compound of claim 10, wherein $R^2$ is $CD_3$.

12. The compound of claim 11, where each $Y^1$ variable is deuterium.

13. The compound of claim 11, where each Z variable is deuterium.

14. The compound of claim 11, where each $Y^1$ and Z variable is deuterium.

15. The compound of claim 11, where each $Y^2$ and $Y^3$ variable is deuterium.

16. The compound of claim 11, where each $Y^2$, $Y^3$ and Z variable is deuterium.

17. The compound of claim 11, where each Y and Z variable is deuterium.

18. A pharmaceutical composition comprising a compound according to any one of claim 1-2, 3-8, 12-9, 10 or 11; and an acceptable carrier.

19. The composition according to claim 18, wherein the composition is suitable for pharmaceutical administration and said carrier is pharmaceutically acceptable.

* * * * *